(12) United States Patent
Liu et al.

(10) Patent No.: US 12,722,021 B2
(45) Date of Patent: Sep. 1, 2026

(54) OZONE CATALYTIC ELIMINATION DEVICE AND PLASMA BEAUTY INSTRUMENT

(71) Applicant: SHENZHEN LEAFLIFE TECHNOLOGY CO., LTD., Shenzhen (CN)

(72) Inventors: Jian Liu, Shenzhen (CN); Jianbo Lin, Shenzhen (CN)

(73) Assignee: SHENZHEN LEAFLIFE TECHNOLOGY CO., LTD., Shenzhen (CN)

( * ) Notice: Subject to any disclaimer, the term of this patent is extended or adjusted under 35 U.S.C. 154(b) by 758 days.

(21) Appl. No.: 18/248,179

(22) PCT Filed: Nov. 9, 2022

(86) PCT No.: PCT/CN2022/130808
§ 371 (c)(1), (2) Date: Apr. 6, 2023

(87) PCT Pub. No.: WO2024/045335
PCT Pub. Date: Mar. 7, 2024

(65) Prior Publication Data

US 2024/0424315 A1 Dec. 26, 2024

(30) Foreign Application Priority Data

Aug. 30, 2022 (CN) ........................ 202211059769.1

(51) Int. Cl.
*A61N 1/44* (2006.01)
*A61N 1/08* (2006.01)
(Continued)

(52) U.S. Cl.
CPC ................ *A61N 1/44* (2013.01); *A61N 1/08* (2013.01); *B01D 53/8675* (2013.01);
(Continued)

(58) Field of Classification Search
CPC ........ A61N 1/44; A61N 1/08; B01D 53/8675; B01D 53/8696; B01D 53/885;
(Continued)

(56) References Cited

U.S. PATENT DOCUMENTS 5,206,002 A * 4/1993 Skelley ................ B01D 53/346 423/393
5,286,447 A * 2/1994 Fannin ...................... F24F 8/26 422/31

(Continued)

FOREIGN PATENT DOCUMENTS

CN 201603070 U 10/2010
CN 205850589 U 1/2017

(Continued)

OTHER PUBLICATIONS

International Search Report and Written Opinion for Corresponding PCT Application No. PCT/CN2022/130808.

*Primary Examiner* — Wesley G Harris
(74) *Attorney, Agent, or Firm* — Bayramoglu Law Offices LLC

(57) ABSTRACT

Provided are an ozone catalytic elimination device and a plasma beauty instrument including the ozone catalytic elimination device. The ozone catalytic elimination device includes an air pumping device, a catalytic device, a heating device, and a cooling device. An air inlet end of the air pumping device is used for communicating with an ionization cavity of the plasma beauty instrument, an air outlet end of the air pumping device communicates with the catalytic device, and ozone generated by the ionization cavity can be pumped to the catalytic device by the air pumping device. The catalytic device is configured to catalyze the ozone into oxygen, the heating device can be configured to heat the ozone, the cooling device communicates with the interior of
(Continued)

the catalytic device, and the cooling device can be configured to cool the oxygen.

18 Claims, 1 Drawing Sheet

(51) Int. Cl.

| | |
|---|---|
| ***B01D 53/86*** | (2006.01) |
| ***B01D 53/88*** | (2006.01) |
| ***H05H 1/24*** | (2006.01) |

(52) U.S. Cl.
CPC ....... *B01D 53/8696* (2013.01); *B01D 53/885* (2013.01); *H05H 1/24* (2013.01); *B01D 2255/2073* (2013.01); *B01D 2255/90* (2013.01); *B01D 2255/9205* (2013.01); *H05H 2245/34* (2021.05); *Y02A 50/20* (2018.01)

(58) Field of Classification Search
CPC ........ B01D 2255/2073; B01D 2255/90; B01D 2255/9205; H05H 1/24; H05H 2245/34; Y02A 50/20; A61L 2/202; A61L 2/14
See application file for complete search history.

(56) References Cited

U.S. PATENT DOCUMENTS

| | | | | |
|---|---|---|---|---|
| 5,334,355 | A * | 8/1994 | Faddis | A61L 2/202 422/177 |
| 5,603,215 | A * | 2/1997 | Sung | B01D 53/944 60/284 |
| 2005/0129571 | A1* | 6/2005 | Centanni | A61L 2/208 422/62 |
| 2011/0117000 | A1* | 5/2011 | Nakatani | B01D 53/8696 422/177 |
| 2011/0262327 | A1* | 10/2011 | Dillon | F23J 15/02 251/304 |
| 2012/0277662 | A1* | 11/2012 | Golkowski | A61L 2/00 422/186.21 |
| 2019/0160529 | A1* | 5/2019 | Silidker | B01D 53/8668 |
| 2020/0315682 | A1 | 10/2020 | Ahn | |

FOREIGN PATENT DOCUMENTS

| | | | | |
|---|---|---|---|---|
| CN | 210584471 | U | 5/2020 | |
| CN | 214862327 | U | 11/2021 | |
| CN | 114099966 | A | 3/2022 | |
| CN | 114459104 | A | 5/2022 | |
| EP | 1538312 | A1 * | 6/2005 | F01N 3/206 |

* cited by examiner

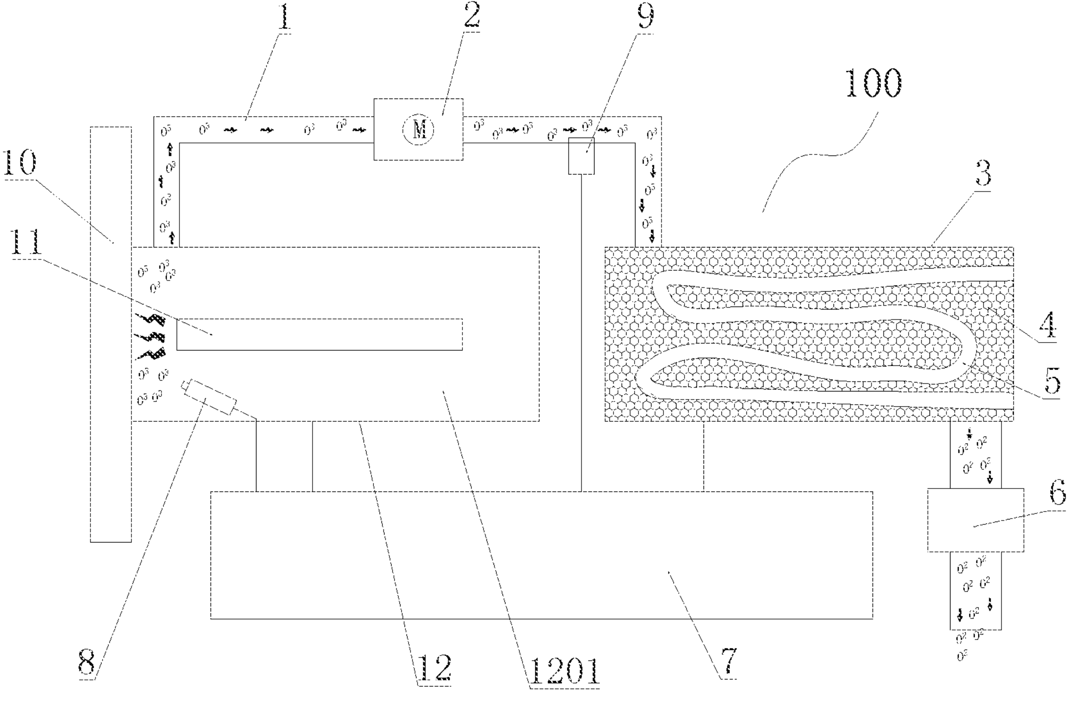
1
2
M
9
100
10
11
3
4
5
6
8
12
1201
7

OZONE CATALYTIC ELIMINATION DEVICE AND PLASMA BEAUTY INSTRUMENT

CROSS-REFERENCE TO RELATED APPLICATION

This patent is a 371 of International Application No. PCT/CN2022/130808, which claims the benefit and priority of Chinese Patent Application No. 202211059769.1, filed with the China National Intellectual Property Administration on Aug. 30, 2022, the disclosure of which is incorporated by reference herein in its entirety as part of the present application.

TECHNICAL FIELD

The present disclosure relates to the technical field of beauty instruments, and in particular to an ozone catalytic elimination device and a plasma beauty instrument.

BACKGROUND

A plasma beauty instrument mainly uses the plasma generator to ionize the air (mainly oxygen) to produce plasma, and then uses the plasma for a beauty treatment. However, the plasma generator may produce ozone gas while generating plasma, and the ozone gas may cause discomfort to operators and beauty consumers, and may cause harm to the bodies of the operators and beauty consumers if they stay in this environment for a long time.

Therefore, how to avoid the harm of ozone to the bodies of operators and beauty consumers has become an urgent problem for those skilled in the art at present.

SUMMARY

To solve the technical problem above, an ozone catalytic elimination device capable of avoiding the harm of ozone to the bodies of operators and beauty consumers as well as a plasma beauty instrument including the ozone catalytic elimination device are provided.

To achieve the objective above, the present disclosure provides the following solutions:

An ozone catalytic elimination device provided by the present disclosure includes an air pumping device, a catalytic device, a heating device, and a cooling device. An air inlet end of the air pumping device is used for communicating with an ionization cavity of the plasma beauty instrument, an air outlet end of the air pumping device communicates with the catalytic device, and ozone generated by the ionization cavity can be pumped to the catalytic device by the air pumping device. The catalytic device can be configured to catalyze the ozone into oxygen, the heating device can be configured to heat the ozone, and the cooling device communicates with the interior of the catalytic device and can be configured to cool the oxygen.

Preferably, the catalytic device includes a first housing and a porous catalytic structure. The porous catalytic structure is arranged inside the first housing, and the air pumping device and the cooling device communicates with both ends of the first housing, respectively. The porous catalytic structure is made of a catalytic structure capable of catalyzing the ozone into the oxygen, and the porous catalytic structure is provided with a plurality of pore channels. Both ends of each pore channel are arranged opposite to both ends of the first housing, respectively.

Preferably, the porous catalytic structure is a honeycomb structure.

Preferably, the catalytic material is manganese oxide.

Preferably, the heating device is arranged inside the first housing.

Preferably, the heating device is a heating pipe.

Preferably, the ozone catalytic elimination device further includes a control element, an ozone concentration detection device, an air velocity detection device, and a temperature detection device. The ozone concentration detection device is arranged at the ionization cavity and is configured to detect the concentration of the ozone in the ionization cavity. The ionization cavity communicates with the catalytic device by an air pumping pipeline, and the air pumping device is arranged on the air pumping pipeline. The air velocity detection device is configured to detect the air velocity inside the air pumping pipeline. The temperature detection device is configured to detect the internal temperature of the first housing. The ozone concentration detection device, the air velocity detection device, the temperature detection device, the air pumping device and the heating device are in communication connection with the control element.

Preferably, the control element is a circuit board.

Preferably, the cooling device includes a second housing, heat exchange metal fins, and a ventilation fan. A heat exchange pipeline is arranged inside the second housing, and communicates with the catalytic device. The heat exchange metal fins are in contact with the heat exchange pipeline to exchange heat with the heat exchange pipeline. The second housing is provided with an air inlet and an air outlet which are in communication with the interior of the second housing; and the ventilation fan is arranged at the air outlet and is configured to exhaust the gas in the second housing.

A plasma beauty instrument is further provided by the present disclosure. The plasma beauty instrument includes the ozone catalytic elimination device, and further includes a main body and a plasma generator. The main body is provided with an ionization cavity, the plasma generator is arranged in the ionization cavity, and an air inlet end of an air pumping device of the ozone catalytic elimination device communicates with the ionization cavity.

Compared with the prior art, the present disclosure obtains the following technical effects:

The ozone catalytic elimination device provided by the present disclosure includes an air pumping device, a catalytic device, a heating device, and a cooling device. An air inlet end of the air pumping device is used for communicating with an ionization cavity of the plasma beauty instrument, an air outlet end of the air pumping device communicates with the catalytic device, and ozone generated by the ionization cavity can be pumped to the catalytic device by the air pumping device. The catalytic device can be configured to catalyze the ozone into oxygen. The heating device can be configured to heat the ozone. The cooling device communicates with the interior of the catalytic device and can be configured to cool the oxygen.

The plasma generator of the plasma beauty instrument is arranged inside the ionization cavity, and one end, in contact with the skin of a beauty consumer, of the ionization cavity is open. During the operation of the plasma beauty instrument, the open end of the ionization cavity of the plasma beauty instrument abuts against the skin of the beauty consumer, the ionization cavity is sealed, and the air in the ionization cavity is ionized by the plasma generator to generate plasma and ozone. The ozone catalytic elimination device is started when the plasma beauty instrument operates, the air pumping device of the ozone catalytic elimination device can pump the gas in the ionization cavity to the catalytic device, the ozone contained in the gas is converted into oxygen under the catalytic action of the catalytic device and the heating of the heating device, and then is exhausted after being cooled by the cooling device. By converting the ozone into the oxygen, the situation that the ozone causes harm to the bodies of operators and beauty consumers is effectively avoided.

BRIEF DESCRIPTION OF THE DRAWINGS

To describe the technical solutions in the embodiments of the present disclosure or in the prior art more clearly, the following briefly introduces the accompanying drawings required for describing the embodiments. Apparently, the accompanying drawings in the following description show merely some embodiments of the present disclosure, and those of ordinary skill in the art may still derive other drawings from these accompanying drawings without creative efforts.

FIG. 1 is a structure diagram of an ozone catalytic elimination device in accordance with an embodiment of the present disclosure.

DETAILED DESCRIPTION OF THE EMBODIMENTS

The following clearly and completely describes the technical solutions in the embodiments of the present disclosure with reference to the accompanying drawings in the embodiments of the present disclosure. Apparently, the described embodiments are merely a part rather than all of the embodiments of the present disclosure. All other embodiments obtained by those of ordinary skill in the art based on the embodiments of the present disclosure without creative efforts shall fall within the protection scope of the present disclosure.

An objective of the present disclosure is to provide an ozone catalytic elimination device capable of avoiding the harm of ozone to the bodies of operators and beauty consumers as well as a plasma beauty instrument including the ozone catalytic elimination device.

To make the objectives, features and advantages of the present disclosure more apparently and understandably, the following further describes the present disclosure in detail with reference to the accompanying drawings and the specific embodiments.

In the drawings: 100—ozone catalytic elimination device; 1—air pumping pipeline; 2—air pumping device; 3—first housing; 4—porous catalytic structure; 5—heating device; 6—cooling device; 7—control element; 8—ozone concentration detection device; 9—air velocity detection device; 10—skin; 11—plasma generator; 12—plasma pipeline; 1201—ionization cavity.

Referring to FIG. 1, an ozone catalytic elimination device provided by this embodiment includes an air pumping device 2, a catalytic device, a heating device 5, and a cooling device 6. An air inlet end of the air pumping device 2 is used for communicating with an ionization cavity 1201 of a plasma beauty instrument, an air outlet end of the air pumping device 2 communicates with the catalytic device, ozone generated by the ionization cavity 1201 can be pumped to the catalytic device by the air pumping device 2, and the catalytic device is configured to catalyze the ozone into oxygen. The heating device 5 can be configured to heat the ozone, and under gaseous conditions, the decomposition rate of the ozone increases rapidly as the temperature rises, and the decomposition rate of the ozone is proportional to the temperature. The cooling device 6 communicates with the interior of the catalytic device, and can be configured to cool the oxygen. During the operation of the plasma beauty instrument, the open end of the ionization cavity 1201 of the plasma beauty instrument abuts against the skin 10 of a beauty consumer, the ionization cavity is sealed, and the air in the ionization cavity 1201 is ionized by the plasma generator 11 to generate plasma and ozone. The ozone catalytic elimination device is started when the plasma beauty instrument operates, the air pumping device 2 of the ozone catalytic elimination device 100 can pump the gas in the ionization cavity 1201 to the catalytic device, the ozone contained in the gas is converted into oxygen under the catalytic action of the catalytic device and the heating of the heating device 5, and then is exhausted after being cooled by the cooling device 6. By converting the ozone into the oxygen, the situation that the ozone causes harm to the bodies of operators and beauty consumers is effectively avoided.

In other preferred embodiments, as shown in FIG. 1, the catalytic device includes a first housing 3 and a porous catalytic structure 4. The porous catalytic structure 4 is arranged inside the first housing 3, and the air pumping device 2 and the cooling device 6 communicates with both ends of the first housing 3, respectively. The porous catalytic structure 4 is made of a catalytic material capable of catalyzing the ozone into oxygen, and the porous catalytic structure 4 is provided with multiple pore channels. Both ends of each pore channel are provided opposite to both ends of the first housing 3, respectively. During specific use, the ozone enters the pore channels and is catalyzed into the oxygen by the porous catalytic structure 4 in the process of passing through the pore channels.

Further, the porous catalytic structure 4 is a honeycomb structure.

Further, the catalytic material is manganese oxide. It should be noted that the catalytic material is not limited to manganese oxide, and may be any other material capable of catalyzing ozone into oxygen.

In other preferred embodiments, the heating device 5 is arranged inside the first housing 3. How the heating device 5 is inside the first housing 3 depends on the actual needs.

In other preferred embodiments, the heating device 5 is a heating pipe. It should be noted that the heating device 5 is not limited to the heating device 5, and may be any other device capable of heating the gas.

In other preferred embodiments, as shown in FIG. 1, the ozone catalytic elimination device 100 further includes a control element 7, an ozone concentration detection device 8, an air velocity detection device 9, and a temperature detection device. The ozone concentration detection device 8 is arranged at the ionization cavity 1201, and is configured to detect the concentration of ozone in the ionization cavity 1201. The ionization cavity 1201 communicates with the catalytic device by an air pumping pipeline 1, and the air pumping device 2 is arranged on the air pumping pipeline 1. The air velocity detection device 9 is configured to detect the air velocity inside the air pumping pipeline 1, and the temperature detection device is configured to detect the internal temperature of the first housing 3. The ozone concentration detection device 8, the air velocity detection device 9, the temperature detection device, the air pumping device 2 and the heating device 5 are in communication connection with the control element 7.

During specific operation, detected ozone concentration information is transmitted, by the ozone concentration detection device 8, to the control element 7; detected air velocity information is transmitted, by the air velocity detection device 9, to the control element 7; and detected internal temperature information of the first housing 3 is transmitted, by the heating device 5, to the control element 7. The control element 7 is configured to adjust the air pumping velocity (the air velocity inside the air pumping pipeline 1) of the air pumping device 2 and the heating temperature of the heating device 5 according to the ozone concentration information, and to monitor the air pumping velocity and the internal temperature of the first housing 3 by the air velocity detection device 9 and the temperature detection device in real time, respectively.

Further, the control element 7 is a circuit board. It should be noted that the control element 7 is not limited to the circuit board, and may be other control structures, e.g., a controller. How to arrange the internal structure of the circuit board belongs to the prior art and does not belong to the focus of protection of the present disclosure, and therefore details will not be described herein again.

Further, the ozone concentration detection device 8 is an ozone concentration sensor, the air velocity detection device 9 is an air velocity sensor, and the temperature detection device is a temperature sensor.

In other preferred embodiments, the cooling device 6 includes a second housing, heat exchange metal fins, and a ventilation fan. A heat exchange pipeline is arranged inside the second housing and communicates with the catalytic device. The heat exchange metal fins are in contact with the heat exchange pipeline to exchange heat with the heat exchange pipeline. The second housing is provided with an air inlet and an air outlet which are in communication with the interior of the second housing; and the ventilation fan is arranged at the air outlet, and is configured to exhaust the gas in the second housing. When the cooling device 6 operates, the external air enters the second housing from the air inlet, and the air, after heat exchange with the heat exchange metal fins, in the second housing, is exhausted from the air outlet under the action of the ventilation fan.

Further, the cooling device 6 also includes an air inlet fan. The air inlet fan is arranged at the air inlet. Under the action of the air inlet fan and the ventilation fan, the air in the second housing can be conveniently and rapidly exchanged with the external air.

Specifically, the heat exchange metal fins are heat exchange copper fins. A copper material has excellent heat-conducting property, and is capable of transferring the heat of the heat exchange pipeline to the heat exchange metal fins.

In other preferred embodiments, the air pumping device 2 is an air pumping fan. It should be noted that the air pumping device 2 is not limited to the air pumping fan, and may be any other devices capable of conveying gas.

It should be noted that the ozone catalytic elimination device 100 provided by the present disclosure is not only applicable to the catalytic elimination of ozone generated in the operation process of the plasma beauty instrument, but also applicable to other occasions where ozone treatment is required, as long as an ozone generating cavity is connected to the air inlet end of the air pumping device 2 during specific use.

The present disclosure further provides a plasma beauty instrument. As shown in FIG. 1, the plasma beauty instrument includes the ozone catalytic elimination device 100 in any of above embodiments, and further includes a main body and a plasma generator 11. The main body is provided with an ionization cavity 1201, and the plasma generator 11 is arranged in the ionization cavity 1201. An air inlet end of an air pumping device 2 of the ozone catalytic elimination device 100 communicates with the ionization cavity 1201.

Further, the main body of the plasma beauty instrument includes a plasma pipeline 12, and the ionization cavity 1201 is formed in the plasma pipeline 12.

Further, the ozone catalytic elimination device 100 is arranged on the main body. During operation, the ozone catalytic elimination device 100 can move as the main body moves.

Several examples are used for illustration of the principles and implementation methods of the present disclosure. The description of the embodiments is merely used to help illustrate the method and its core principles of the present disclosure. In addition, those of ordinary skill in the art can make various modifications in terms of specific embodiments and scope of application in accordance with the teachings of the present disclosure. In conclusion, the content of this specification shall not be construed as a limitation to the present disclosure.

What is claimed is:

1. An ozone catalytic elimination device, comprising:
an air pumping device;
a catalytic device;
a heating device; and a cooling device,
wherein:
an air inlet end of the air pumping device is configured to communicate with an ionization cavity of the ozone catalytic elimination device;
an air outlet end of the air pumping device is configured to communicate with the catalytic device; and
the air pumping device is configured to pump, to the catalytic device, ozone generated by the ionization cavity, and
wherein the catalytic device is configured to catalyze the ozone into oxygen, the heating device is configured to heat the ozone, the cooling device communicates with an interior of the catalytic device, and the cooling device is configured to cool the oxygen;
wherein the catalytic device comprises:
a first housing; and
a porous catalytic structure,
wherein the porous catalytic structure is disposed within the first housing,
wherein the air pumping device and the cooling device are configured to communicate with both ends of the first housing, respectively,
wherein the porous catalytic structure comprises a catalytic structure capable of catalyzing the ozone into the oxygen;
wherein the porous catalytic structure includes a plurality of pore channels, and both ends of each pore channel are arranged opposite to both ends of the first housing, respectively; and
wherein the heating device is disposed within the first housing.

2. The ozone catalytic elimination device according to claim 1, wherein the porous catalytic structure comprises a honeycomb structure.

3. The ozone catalytic elimination device according to claim 1, wherein the porous catalytic structure includes a catalytic material comprising manganese oxide.

4. The ozone catalytic elimination device according to claim 1, wherein the heating device comprises a heating pipe.

5. The ozone catalytic elimination device according to claim 1, further comprising:

a control element;

an ozone concentration detection device:

an air velocity detection device, wherein the ozone concentration detection device is disposed within the ionization cavity and is configured to detect a concentration of the ozone in the ionization cavity, wherein the ionization cavity communicates with the catalytic device by an air pumping pipeline, and the air pumping device is arranged on the air pumping pipeline, wherein the air velocity detection device is configured to detect an air velocity inside the air pumping pipeline, and wherein the ozone concentration detection device, the air velocity detection device, the air pumping device and the heating device are communicatively coupled with the control element.

6. The ozone catalytic elimination device according to claim 5, wherein the control element comprises a circuit board.

7. The ozone catalytic elimination device according to claim 1, wherein the cooling device comprises:

a second housing;

wherein the second housing is provided with an air inlet and an air outlet which are in communication with an interior of the second housing.

8. The ozone catalytic elimination device according to claim 1, wherein the heating device comprises a heating pipe.

9. A plasma beauty instrument, comprising:

an ozone catalytic elimination device, the ozone catalytic elimination device comprising:

an air pumping device;

a catalytic device;

a heating device; and a cooling device;

a main body; and a plasma generator, wherein the main body is provided with an ionization cavity, the plasma generator is disposed within the ionization cavity, and an air inlet end of the air pumping device of the ozone catalytic elimination device is configured to communicate with the ionization cavity, wherein an air outlet end of the air pumping device is configured to communicate with the catalytic device, and wherein the air pumping device is configured to pump, to the catalytic device, ozone generated by the ionization cavity, and wherein the catalytic device is configured to catalyze the ozone into oxygen, the heating device is configured to heat the ozone, the cooling device communicates with an interior of the catalytic device, and the cooling device is configured to cool the oxygen.

10. The plasma beauty instrument according to claim 9, wherein the catalytic device comprises:

A first housing; and a porous catalytic structure, wherein the porous catalytic structure is disposed within the first housing, wherein the air pumping device and the cooling device is configured to communicate with both ends of the first housing, respectively, wherein the porous catalytic structure is made of a catalytic structure capable of catalyzing the ozone into the oxygen, and wherein the porous catalytic structure is provided with a plurality of pore channels, and both ends of each pore channel are arranged opposite to both ends of the first housing, respectively.

11. The plasma beauty instrument according to claim 10, wherein the porous catalytic structure comprises a honeycomb structure.

12. The plasma beauty instrument according to claim 10, wherein the porous catalytic structure includes a catalytic material comprising manganese oxide.

13. The plasma beauty instrument according to claim 10, wherein the heating device is disposed within the first housing.

14. The plasma beauty instrument according to claim 13, wherein the heating device comprises a heating pipe.

15. The plasma beauty instrument according to claim 13, further comprising:

a control element;

an ozone concentration detection device:

an air velocity detection device;

wherein the ozone concentration detection device is disposed within the ionization cavity and is configured to detect a concentration of the ozone in the ionization cavity, wherein the ionization cavity is configured to communicate with the catalytic device by an air pumping pipeline, wherein the air pumping device is disposed on the air pumping pipeline, wherein the air velocity detection device is configured to detect an air velocity inside the air pumping pipeline, wherein the ozone concentration detection device, the air velocity detection device, the air pumping device and the heating device are communicatively coupled with the control element.

16. The plasma beauty instrument according to claim 15, wherein the control element comprises a circuit board.

17. The plasma beauty instrument according to claim 9, wherein the heating device comprises a heating pipe.

18. The plasma beauty instrument according to claim 9, wherein the cooling device comprises:

a second housing;

wherein the second housing is provided with an air inlet and an air outlet which are in communication with an interior of the second housing.

* * * * *